US009823262B2

(12) United States Patent
Yoshida et al.

(10) Patent No.: US 9,823,262 B2

(45) Date of Patent: Nov. 21, 2017

(54) CONTAINER INSPECTION DEVICE

(71) Applicants: Kabushiki Kaisha N-Tech, Gifu-ken (JP); Kabushiki Kaisha Yakult Honsha, Tokyo (JP); Tohoshoji Kabushiki Kaisha, Osaka (JP)

(72) Inventors: Osamu Yoshida, Gifu-ken (JP); Chizuka Kai, Tokyo (JP); Kunimitsu Toyoshima, Osaka (JP)

(73) Assignees: KABUSHIKI KAISHA N-TECH, Gifu-ken (JP); KABUSHIKI KAISHA YAKULT HONSHA, Tokyo (JP); TOHOSHOJI KABUSHIKI KAISHA, Osaka (JP)

( * ) Notice: Subject to any disclaimer, the term of this patent is extended or adjusted under 35 U.S.C. 154(b) by 0 days.

(21) Appl. No.: 15/315,373

(22) PCT Filed: Jun. 4, 2015

(86) PCT No.: PCT/JP2015/066166

§ 371 (c)(1),
(2) Date: Nov. 30, 2016

(87) PCT Pub. No.: WO2015/186778

PCT Pub. Date: Dec. 10, 2015

(65) Prior Publication Data

US 2017/0199213 A1 Jul. 13, 2017

(30) Foreign Application Priority Data

Jun. 5, 2014 (JP) ................................ 2014-116861

(51) Int. Cl.
*B65B 57/00* (2006.01)
*B65G 47/00* (2006.01)
(Continued)

(52) U.S. Cl.
CPC ............ *G01N 35/04* (2013.01); *B65B 57/00* (2013.01); *B65G 15/00* (2013.01); *B65G 25/02* (2013.01)

(58) Field of Classification Search
None
See application file for complete search history.

(56) References Cited

U.S. PATENT DOCUMENTS 5,618,990 A 4/1997 Iwao et al.
7,946,429 B2 * 5/2011 Kennedy .................. B07C 5/38 198/456
2008/0066525 A1 3/2008 Kojima et al.

FOREIGN PATENT DOCUMENTS

JP 60-127438 A 7/1985
JP 7-242218 A 9/1995
(Continued)

OTHER PUBLICATIONS

International Preliminary Report on Patentability,PCT/JP2015/06616, dated Dec. 6, 2016.

*Primary Examiner* — Kavel Singh

(57) ABSTRACT

A container inspection device includes an inlet conveyor, an outlet conveyor, a mounting table having a mounting surface, a chamber portion having an opening in a section of the chamber portion, in which a receiving space is formed when the mounting surface contacts the chamber portion to close the opening, and a transfer. The transfer is movable in the certain direction at a speed greater than the conveying speed of the cartons by the inlet conveyor. The transfer holds multiple ones of the cartons that have been conveyed by the inlet conveyor collectively and conveys the cartons to the mounting surface of the mounting table, and holds the multiple ones of the cartons mounted on the mounting surface collectively and conveys the cartons to the outlet conveyor.

5 Claims, 6 Drawing Sheets

(51) Int. Cl.

| | |
|---|---|
| ***B65G 47/31*** | (2006.01) |
| ***B65G 15/00*** | (2006.01) |
| ***B65G 47/30*** | (2006.01) |
| ***G01N 35/04*** | (2006.01) |
| ***B65G 25/02*** | (2006.01) |

(56) References Cited

FOREIGN PATENT DOCUMENTS

| | | | |
|---|---|---|---|
| JP | 8-80918 | A | 3/1996 |
| JP | 3-167434 | A | 7/1997 |
| JP | 2006-8161 | A | 1/2006 |

* cited by examiner

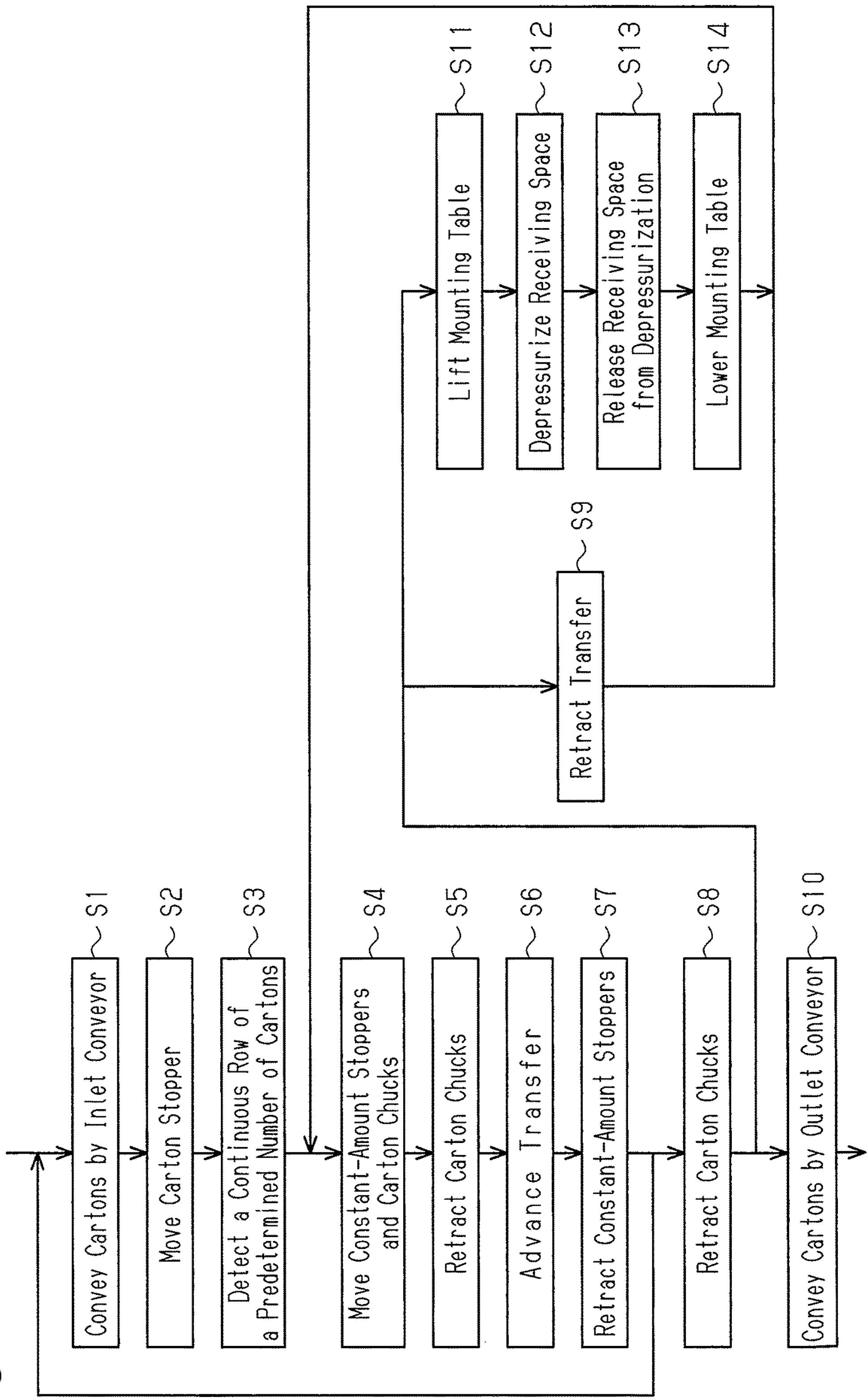
Fig.3
Convey Cartons by Inlet Conveyor
S1
Move Carton Stopper
S2
Detect a Continuous Row of a Predetermined Number of Cartons
S3
Move Constant-Amount Stoppers and Carton Chucks
S4
Retract Carton Chucks
S5
Advance Transfer
S6
Retract Constant-Amount Stoppers
S7
Retract Carton Chucks
S8
Convey Cartons by Outlet Conveyor
S10
Retract Transfer
S9
Lift Mounting Table
S11
Depressurize Receiving Space
S12
Release Receiving Space from Depressurization
S13
Lower Mounting Table
S14

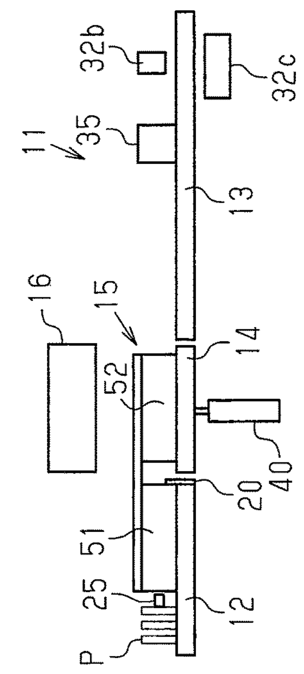
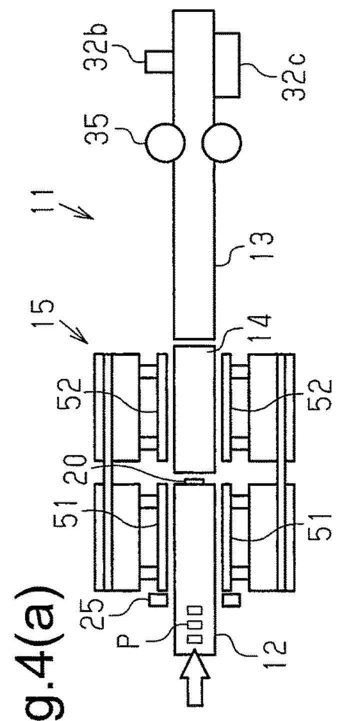
Fig.4(a)
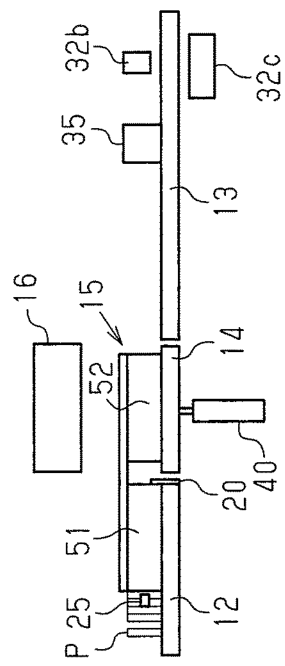
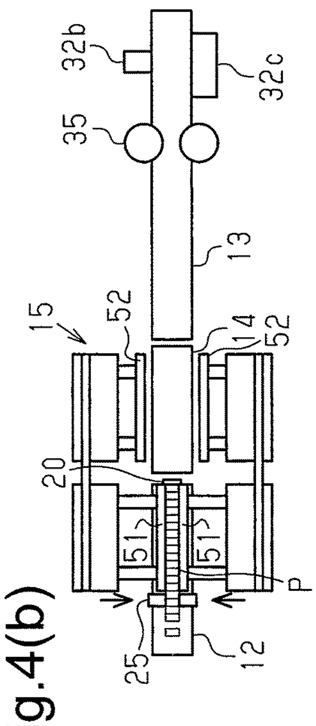
Fig.4(b)
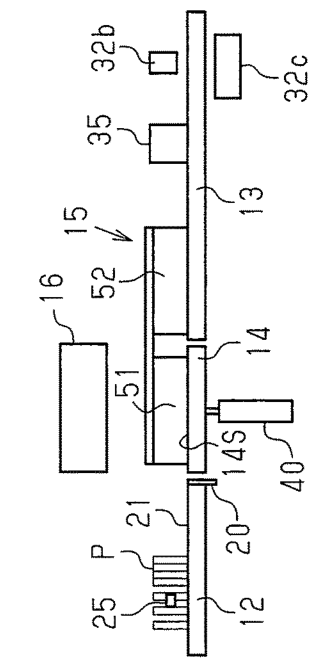
Fig.4(c)

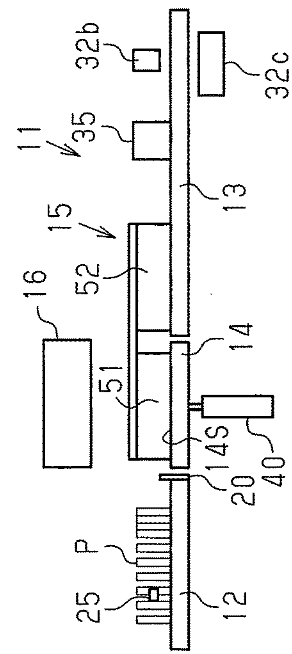
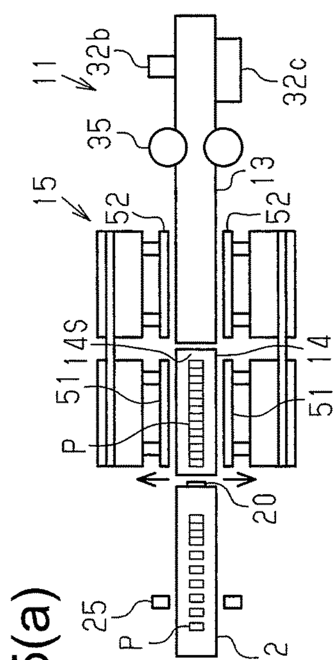
Fig.5(a)
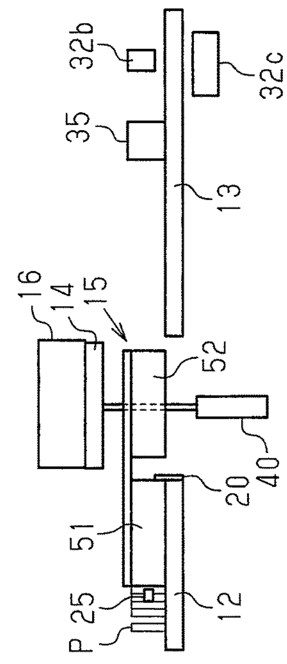
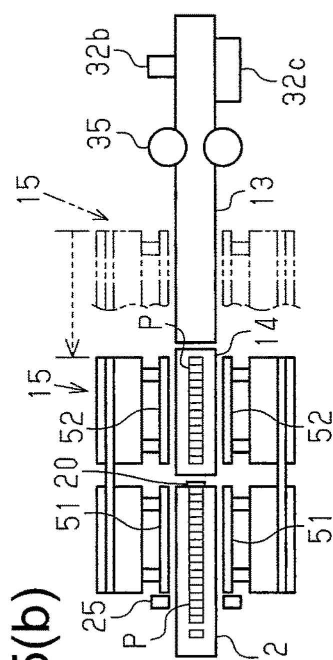
Fig.5(b)
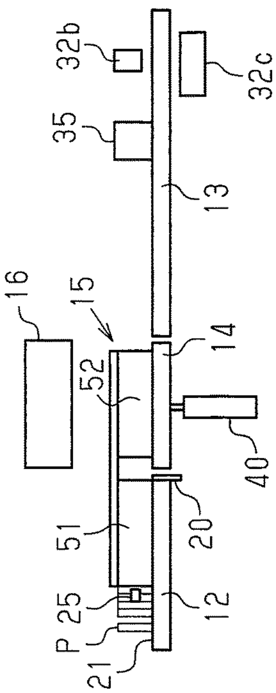
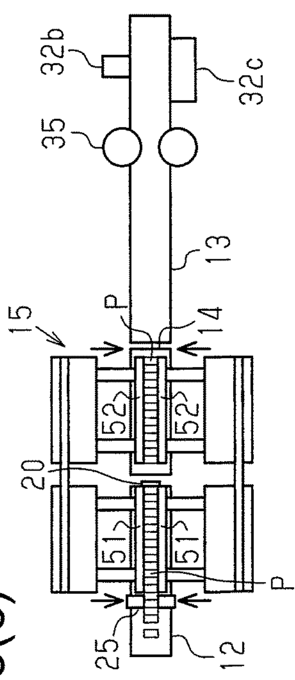
Fig.5(c)

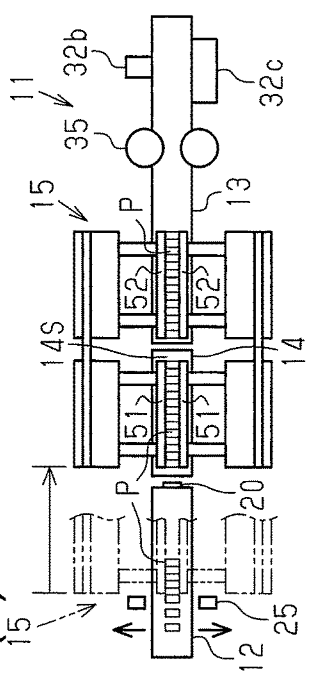
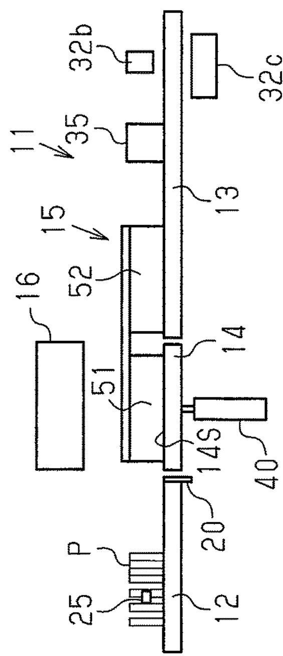
Fig.6(a)
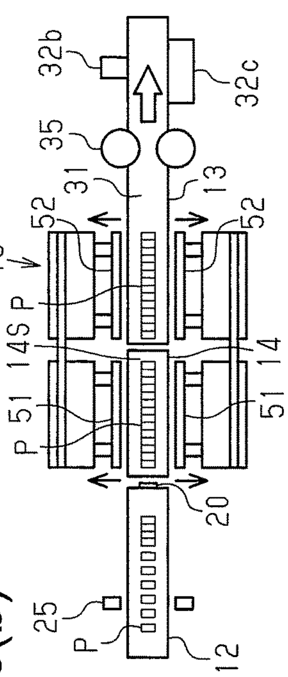
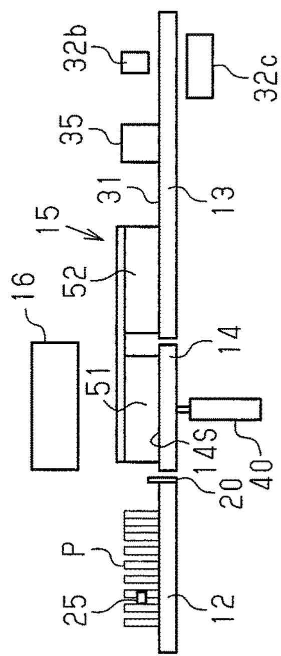
Fig.6(b)
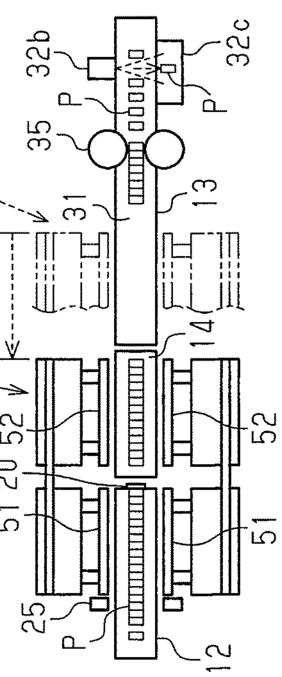
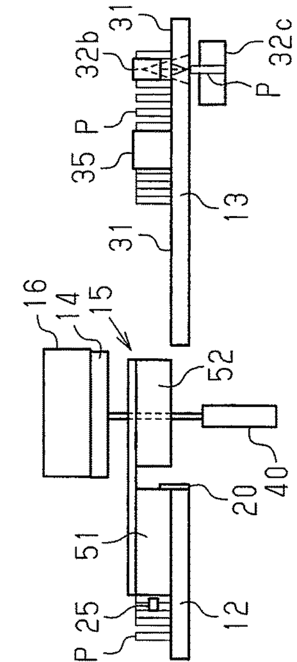
Fig.6(c)

CONTAINER INSPECTION DEVICE

TECHNICAL FIELD

The present invention relates to a container inspection device that inspects a conveyed container while the container is conveyed.

BACKGROUND ART

Conventionally, there is a container inspection device that inspects a flexible liquid container, such as a paper carton or a transfusion bag, which contains liquid, for excessive trapped air at the time the container is conveyed by a conveying means. The container inspection device receives a conveyed liquid container in a sealed space and depressurizes the sealed space. If an outer wall of the container expands, the container inspection device determines that the container has excessive trapped air. Therefore, the time needed for receiving the container in the sealed space and the time needed for depressurizing the sealed space may increase the inspection time of the liquid container.

Accordingly, to solve this problem, a certain conventionally proposed container inspection device receives a plurality of liquid containers in a receiving case having a sealable receiving space and has a plurality of such receiving cases to restrain increase of the inspection time per liquid container. That is, in this conventional container inspection device, the multiple receiving cases are arranged and separately moved such that the receiving cases become connected to a conveying means alternately or sequentially. Then, multiple liquid containers (multiple inspection targets) are conveyed by the conveying means and sequentially received in the sealable receiving spaces of the receiving cases that have been connected to the conveying means alternately or sequentially. The multiple liquid containers (the multiple inspection targets) are then sequentially discharged from the receiving spaces by the conveying means (see, for example, Patent Document 1).

PRIOR ART DOCUMENT

Patent Document

Patent Document 1: Japanese Laid-Open Patent Publication No. 2006-8161

SUMMARY OF THE INVENTION

Problems that the Invention is to Solve

To decrease the inspection time per liquid container by the conventional container inspection device, the conveying speed of each liquid container by the conveying means must be increased to decrease the time needed for receiving multiple liquid containers in a corresponding one of the receiving cases. Also, the movement speed of each receiving case at the time the receiving cases are moved to be connected to the conveying means alternately or sequentially must be increased.

However, if the conveying speed of each liquid container is increased, the liquid containers move at a high speed in the corresponding receiving spaces after having been conveyed. The liquid containers are thus likely to strike one another and fall in the receiving spaces. This hampers accurate inspection for excessive trapped air in the liquid containers. Also, if the movement speed of each receiving case is increased, a great drive force becomes necessary to move each receiving case with multiple liquid containers received in the sealable receiving space. This makes it difficult to increase the movement speed of each receiving case.

The aforementioned facts are generally common in container inspection devices in which multiple liquid containers that are conveyed are received and inspected in a receiving space.

Accordingly, to solve the above-described problems, it is an objective of the present invention to provide a container inspection device capable of decreasing the inspection time per liquid container for multiple liquid containers that are conveyed.

Means for Solving the Problems

Means for solving the above-described problems and operation and effects of the means will hereafter be described.

A container inspection device that solves the above-described problem is a container inspection device that receives and inspects a plurality of conveyed liquid containers in a receiving space. The container inspection device includes a first conveying portion that conveys the liquid containers containing a liquid in a certain direction, a second conveying portion that is arranged downstream from the first conveying portion in the certain direction and conveys the liquid containers in the certain direction, a mounting table that is arranged between the first conveying portion and the second conveying portion and has a mounting surface on which multiple ones of the liquid containers can be mounted, a receiving case having an opening in a section of the receiving case in which the receiving space is formed when the mounting surface contacts the receiving case to close the opening, and a third conveying portion that is movable in the certain direction at a speed greater than a conveying speed of the liquid containers by the first conveying portion, holds multiple ones of the liquid containers that have been conveyed by the first conveying portion collectively and conveys the liquid containers to the mounting surface of the mounting table, and holds the multiple ones of the liquid containers mounted on the mounting surface collectively and conveys the liquid containers to the second conveying portion.

In this configuration, the third conveying portion conveys the multiple liquid containers from the first conveying portion to the mounting table at a high speed and from the mounting table to the second conveying portion at a high speed. This increases the conveying speed of the liquid containers before and after the liquid containers mounted on the mounting table are inspected in the receiving space. The inspection time per liquid container is thus decreased.

In the container inspection device, it is preferable that the first conveying portion, the second conveying portion, and the mounting table be aligned in a row in the certain direction.

This configuration allows the third conveying portion to convey the liquid containers from the first conveying portion to the second conveying portion via the mounting table by a minimum distance. This decreases the inspection time per liquid container.

It is preferable that the container inspection device include a conveying stopping portion that stops conveyance of the liquid containers by the first conveying portion and arranges multiple ones of the liquid containers in a continuous row in the certain direction and that the third conveying portion hold the multiple ones of the liquid containers arranged in the continuous row collectively and convey the liquid containers to the mounting surface of the mounting table.

In this configuration, the third conveying portion conveys the multiple ones of the liquid containers that have been arranged in the continuous row by the first conveying portion while maintaining the liquid containers in the continuous row. This ensures high-speed conveying of the liquid containers from the first conveying portion to the mounting table, without increasing the conveying speed of the liquid containers by the first conveying portion. The inspection time per liquid container is thus decreased.

In the container inspection device, it is preferable that the mounting surface of the mounting table be movable and that the mounting surface move to contact the receiving case and close the opening, thereby forming the receiving space.

In this configuration, the receiving space of the liquid containers is formed by moving the mounting surface without moving the receiving case. This facilitates high-speed movement of multiple liquid containers into the receiving space compared to a case in which the receiving case is moved. Decrease of the inspection time per liquid container is thus facilitated.

In the container inspection device, it is preferable that the mounting surface of the mounting table can be selectively lifted and lowered in a vertical direction and that the mounting surface be lifted to contact the receiving case having a downward opening from below, thereby closing the opening to form the receiving space.

In this configuration, the mounting table (the mounting surface) and the receiving case are located at the positions layered in the up-down direction. This restrains increase of the surface area occupied by the container inspection device in a horizontal direction and decreases the inspection time per liquid container.

BRIEF DESCRIPTION OF THE DRAWINGS

FIG. 3 is a flowchart representing carton inspecting operation performed by the container inspection device.

FIGS. 4(*a*), 4(*b*), and 4(*c*) are diagrams each representing a state of the container inspection device at the time the device is in the carton inspecting operation.

FIGS. 5(*a*), 5(*b*), and 5(*c*) are diagrams each representing a state of the container inspection device at the time the device is in the carton inspecting operation.

FIGS. 6(*a*), 6(*b*), and 6(*c*) are diagrams each representing a state of the container inspection device at the time the device is in the carton inspecting operation.

MODE FOR CARRYING OUT THE INVENTION

An embodiment of a container inspection device will now be described with reference to the attached drawings. The container inspection device of the embodiment is a container inspection device in which a plurality of paper cartons each serving as an example of a liquid container, which contains milk as an example of the liquid, are received in a receiving space and subjected to a predetermined inspection at the time the cartons are conveyed. The liquid container may be any other flexible liquid container, such as a paper or plastic carton containing any liquid other than milk or a transfusion bag.

Figure 1A:
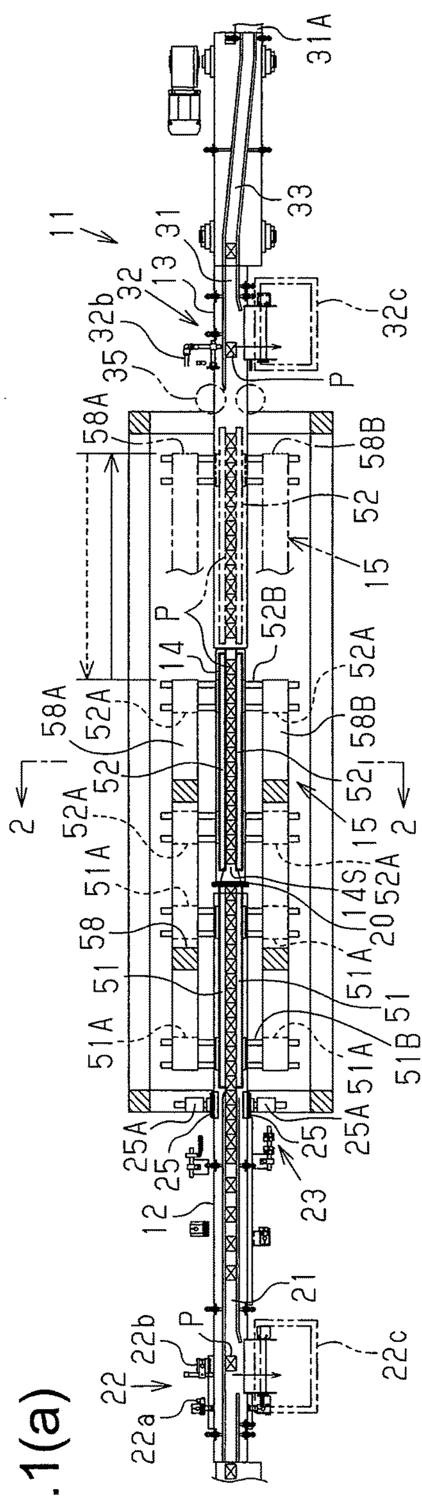
FIGS. 1(*a*) and 1(*b*) are a plan view and a front view, respectively, schematically showing the configuration of a container inspection device according to an embodiment.
Figure 1B:
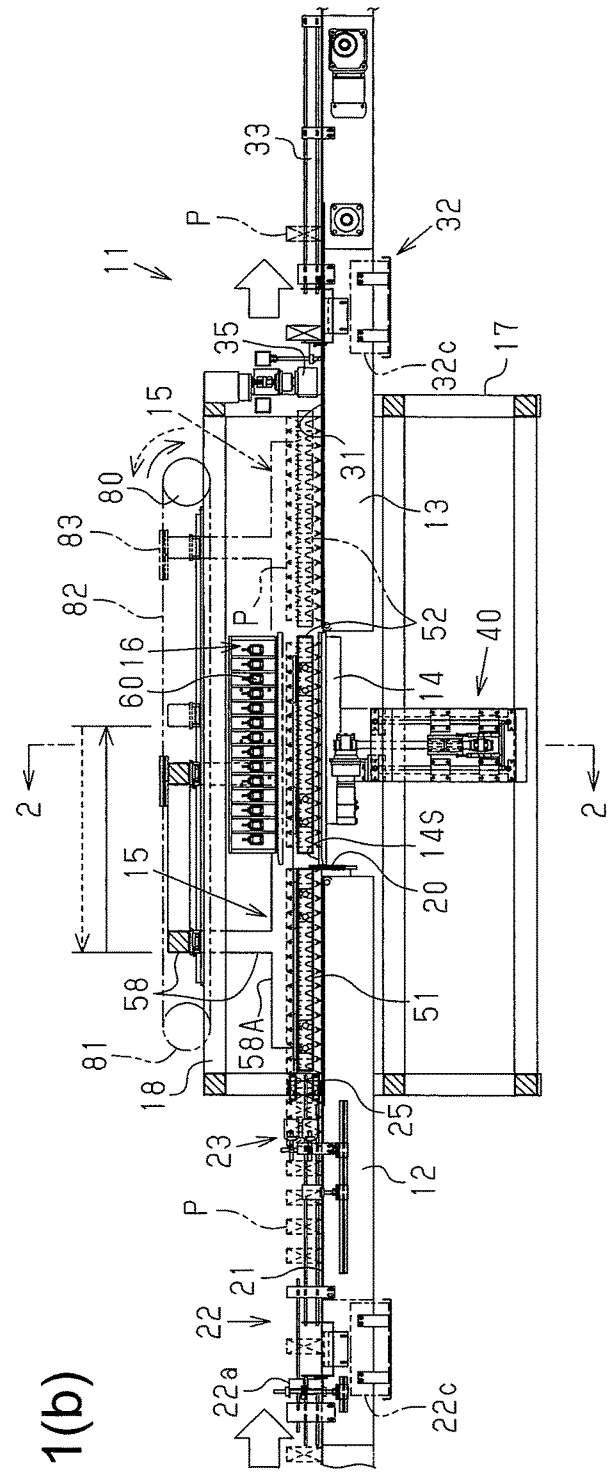

As illustrated in FIGS. 1(*a*) and 1(*b*), a container inspection device 11 includes an inlet conveyor 12 serving as a first conveying portion, which conveys cartons P containing milk in a certain direction, and an outlet conveyor 13 serving as a second conveying portion, which is arranged downstream from the inlet conveyor 12 in the certain direction and conveys the cartons P in the certain direction. A mounting table 14, which has a mounting surface 14S on which multiple ones of the cartons P can be mounted, is arranged between the inlet conveyor 12 and the outlet conveyor 13. In the illustrated embodiment, the certain direction is a horizontal direction. The inlet conveyor 12, the outlet conveyor 13, and the mounting table 14 are aligned in a row in the certain direction.

A chamber portion 16 having a downward opening 16K (see FIG. 2), which is an example of a receiving case, is located at an upper side, which is the antigravity side in the vertical direction with respect to the mounting table 14. The chamber portion 16 is a component configuring a device frame body 17 shaped as a rectangular parallelepiped and is fixed to a transverse bar 18, which extends in the certain direction. For illustrative purposes, FIG. 1(*a*) represents the container inspection device 11 in a state in which an upper section of the device frame body 17 including the chamber portion 16 is removed (cut away).

The mounting table 14 is a plate member shaped substantially as a rectangular parallelepiped and movable in an up-down direction by means of a lift mechanism 40, which is fixed to the device frame body 17. The mounting table 14 is moved upward (lifted) such that the mounting surface 14S is pressed against and contacts the chamber portion 16 from below and closes the opening 16K, thus forming a receiving space SK (see FIG. 2), which is capable of receiving cartons P, in the chamber portion 16. That is, by lifting the mounting table 14 from its initial position, multiple cartons P mounted on the mounting surface 14S are received in the receiving space SK. By lowering the mounting table 14 to the initial position such that the mounting surface 14S becomes separate from the opening 16K of the chamber portion 16, the cartons P mounted on the mounting surface 14S are withdrawn from the received space SK in the chamber portion 16. In the illustrated embodiment, the mounting surface 14S and the opening 16K each have a rectangular shape in which the certain direction is the longitudinal direction. The cartons P are mounted on the mounting surface 14S in a state aligned in the certain direction.

A non-illustrated vacuum pump is connected to the chamber portion 16 with respect to the receiving space SK formed in the chamber portion 16 via a non-illustrated line allowing air communication. That is, in the illustrated embodiment, the receiving space SK formed in the chamber portion 16 is a sealed space and can be depressurized to a certain pressure through actuation of the vacuum pump.

The container inspection device 11 includes a transfer 15 serving as a third conveying portion capable of reciprocating in the certain direction, which is the longitudinal direction of the transverse bar 18, as represented by the solid arrow and the broken arrow in each of FIGS. 1(*a*) and 1(*b*). The transfer 15 has a movable frame body 58 capable of sliding while being guided by a guide rail 18G (see FIG. 2), which is arranged in the transverse bar 18 of the device frame body 17, and a pair of opposing first carton chucks 51 and a pair of opposing second carton chucks 52, which are arranged in the movable frame body 58.

A section of the movable frame body 58 is attached to an endless belt 82, which is wound around a pair of rollers 80, 81, by means of a fixing portion 83. When driven by a drive source such as a motor, at least one of the rollers 80, 81 rolls as represented by the solid arrow or the broken arrow of FIG. 1(*b*). Through such rolling of the roller(s) 80, 81, the movable frame body 58, or, that is, the transfer 15, is allowed to reciprocate in the certain direction at a speed greater than the conveying speed of the cartons P by the inlet conveyor 12, as represented by the long dashed double-short dashed line in each of FIGS. 1(*a*) and 1(*b*).

The two first carton chucks 51 and the two second carton chucks 52 are movable each in a direction crossing the certain direction. Each pair of the first and second carton chucks 51, 52 is arranged at such a position that, by moving from the initial positions toward the opposing carton chucks 51, 52 with respect to the movable frame body 58, the respective pairs of the first and second carton shucks 51, 52 can clamp and hold corresponding multiple cartons P collectively.

Therefore, the first carton chucks 51 hold the corresponding cartons P, which have been conveyed by the inlet conveyor 12, collectively and convey the cartons P to the mounting surface 14S of the mounting table 14. The second carton chucks 52 hold the cartons P mounted on the mounting surface 14S collectively and convey the cartons P to the outlet conveyor 13. That is, the transfer 15 is capable of conveying multiple cartons P collectively in the certain direction.

A conveyor belt 21, which conveys the cartons P mounted on a belt surface, is arranged in the inlet conveyor 12. A carton stopper 20, which moves from its initial position in a manner projecting upward with respect to the belt surface of the conveyor belt 21 through actuation of a non-illustrated actuator, is arranged in a finishing end section of the conveying path formed by the conveyor belt 21 in the certain direction. The carton stopper 20 functions as a conveying stopping portion that prevents and stops movement of the cartons P conveyed in the certain direction through the above-described projecting movement, thus arranging the cartons P in a continuous row in which the cartons P are continuous in the certain direction.

The inlet conveyor 12 includes a pair of constant-amount stoppers 25, which is capable of reciprocating in a direction crossing the certain direction. Through actuation of corresponding actuators 25A, the constant-amount stoppers 25 move from their initial positions to clamp cartons P from opposite sides and hold at least one of the cartons P. When the transfer 15 moves in the certain direction, the constant-amount stoppers 25 stop cartons P from being conveyed to a downstream side in the conveying direction, or, in other words, in the certain direction, by the conveyor belt 21 of the inlet conveyor 12.

The inlet conveyor 12 includes a posture sensor 22*a*, which detects the posture of a conveyed carton P, and a carton removal mechanism 22, by which, based on a detection result of the posture sensor 22*a*, a carton P in an undesirable posture is dropped into a removal case 22*c* by using gas (air) blasted from a blasting portion 22*b* and is thus removed. Further, the inlet conveyor 12 has a continuous-row detecting portion 23. When cartons P that have been stopped by the projected carton stopper 20 from moving (being conveyed) form a continuous row of a predetermined number of cartons P on the inlet conveyor 12, the continuous-row detecting portion 23 detects the rearmost carton P of the continuous row of the cartons P at the upstream side in the conveying direction by means of a sensor.

On the other hand, the outlet conveyor 13 has a conveyor belt 31, which conveys the multiple cartons P that have been conveyed collectively by the transfer 15 and mounted onto a belt surface of the conveyor belt 31 in the certain direction. A stabilizer 35, which is configured by a pair of rotational bodies that rotates at a relatively small circumferential speed with respect to the movement speed of the conveyor belt 31, is arranged on the conveyor belt 31. That is, the stabilizer 35 causes the cartons P, which are conveyed in a continuous row, to be conveyed in a state spaced apart on the outlet conveyor 13.

The outlet conveyor 13 also has a carton discharge mechanism 32, by which those of the conveyed cartons P that have been determined to have excessive trapped air inside by inspection in the receiving space SK in the chamber portion 16 are discharged from the conveyor belt 31 into a discharge case 32*c* by using gas (air) blasted from a blasting portion 32*b*. Further, to change the conveying speed of each carton P in the certain direction, the outlet conveyor 13 includes another conveyor belt 31A, which moves at a speed different from the speed of the conveyor belt 31, in addition to the conveyor belt 31. A movement line 33 is arranged to move cartons P onto a belt surface of the conveyor belt 31A.

Figure 2:
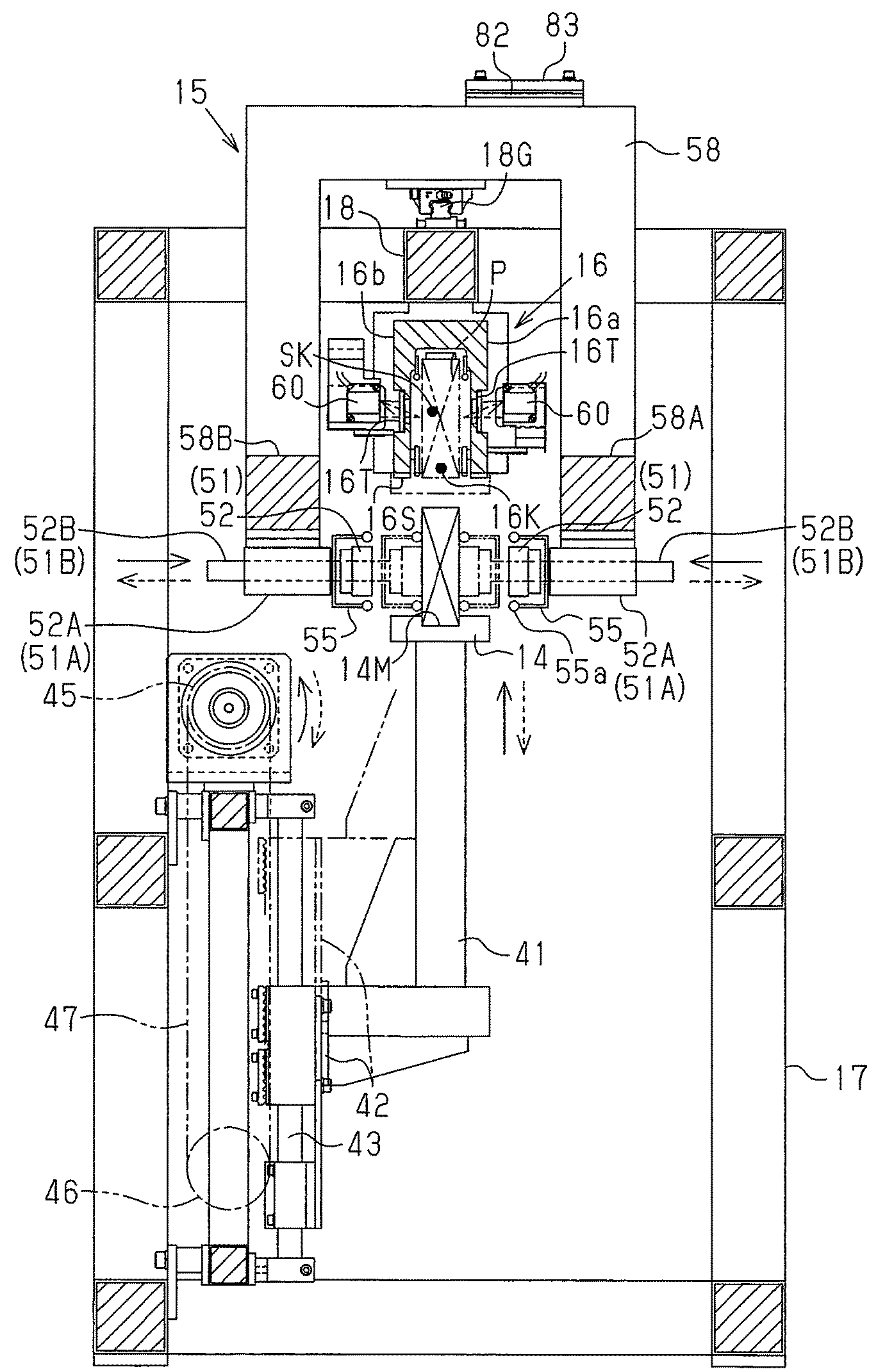
FIG. 2 is a cross-sectional view taken along arrows 2-2 of FIGS. 1(*a*) and 1(*b*).

The configurations of the mounting table 14, the chamber portion 16, and the transfer 15 will hereafter be described with reference to FIG. 2.

A rectangular support post 41 is fixed to a lower side of the mounting table 14. The support post 41 is also fixed to a base 42 in an upright state. The base 42 is movable in the up-down direction by being guided by a guide shaft 43, which has a vertical axis. The base 42 is attached to a section of a drive belt 47, which is wound around a pair of pulleys 45, 46 rotated through operation of a drive source such as a motor. Therefore, through rotation of the pulleys 45, 46, the mounting table 14 is selectively lifted and lowered as represented by the solid arrow and the broken arrow in FIG. 2. In the mounting surface 14S of the mounting table 14, the mounting portion on which cartons P are mounted is a groove portion 14M. The groove portion 14M restrains movement of the cartons P mounted on the mounting surface 14S in a horizontal direction crossing the certain direction (as viewed in FIG. 2, a transverse direction of the sheet surface).

The chamber portion 16 is capable of receiving a plurality of cartons P (in the illustrated embodiment, a maximum of fourteen cartons P (see FIG. 1)) that are in a continuous row in the certain direction. The chamber portion 16 is shaped as a box with a bottom, in which a receiving space SK having the downward opening 16K in a section of the receiving space SK is formed. The bottom of the box shape of the chamber portion 16 is located at the upper side and fixed to the transverse bar 18 of the device frame body 17. An elastically deformable packing 16S is attached to the periphery of the opening 16K, which faces downward. When the mounting table 14 is lifted such that the mounting surface 14S contacts the chamber portion 16, the packing 16S closes the opening 16K. This seals the gap between the mounting surface 14S and the chamber portion 16, thus causing the receiving space SK to become a sealed space.

A transmitting portion 16T is formed along each longitudinal side wall section 16*a*, 16*b* of the chamber portion 16, which configures the corresponding long side of the opening 16K. A transmitting member through which a predetermined light ray is transmitted is attached, in an airtight state, to each of the transmitting portions 16T. The light ray is emitted onto the respective cartons P received in the receiving space SK through the transmitting portions 16T. Based on the time from when the light ray is emitted to when the light ray is returned after having been reflected by each of the cartons P, the displacement amount of each of the opposite side surfaces of the carton P received in the receiving space SK is detected. For this purpose, in the chamber portion 16, a maximum of fourteen displacement sensors 60 (for example, photoelectric sensors), each of which detects the displacement amount of the corresponding side surface of the corresponding one of the cartons P, are attachable to either the longitudinal side wall portion 16*a* or the longitudinal side wall portion 16*b* in correspondence with the respective cartons P. In other words, a total of twenty-eight displacement sensors 60 are attachable for both of the longitudinal side wall portions 16*a*, 16*b* in the chamber portion 16 (see FIG. 1(*b*)).

With reference to FIGS. 1(*a*) and 2, the transfer 15 includes two support members 58A, 58B, each of which extends linearly in the certain direction and has a square cross section, in the movable frame body 58, which is supported by the transverse bar 18 of the device frame body 17 and is slidable, such that the support members 58A, 58B are located at opposite sides of the mounting table 14 as viewed from above. Two first actuators 51A are attached to each of the support members 58A, 58B at the trailing side in the certain direction with respect to a middle section of the support member 58A, 58B. Two second actuators 52A are attached to each support member 58A, 58B at the leading side in the certain direction with respect to the middle section of the support member 58A, 58B.

Each of the two first actuators 51A and each of the two second actuators 52A include a plurality of moving rods 51B and a plurality of moving rods 52B, respectively. The moving rods 51B, 52B are capable of reciprocating in a direction crossing the certain direction, as represented by the solid arrows and the broken arrows in FIG. 2. Each of the first carton chucks 51 is attached to the front end sections of the corresponding ones of the moving rods 51B. Each of the second carton chucks 52 is attached to the front end sections of the corresponding ones of the moving rods 52B. That is, the transfer 15 has a pair of (two) first carton chucks 51 and a pair of (two) second carton chucks 52 such that each of the first and second carton chucks 51, 52 opposes the corresponding one of the first and second carton chucks 51, 52 in a direction crossing the certain direction as viewed from above (see FIG. 1(*a*)).

By simultaneously actuating the total of four first actuators 51A, which are attached to the two support members 58A, 58B, the two first carton chucks 51 are moved toward each other with respect to their initial positions. Such movement brings the first carton chucks 51 into contact with the corresponding cartons P in a clamping manner. The first carton chucks 51 thus hold the multiple cartons P conveyed by the inlet conveyor 12 collectively. Also, by simultaneously actuating the total of four second actuators 52A, which are attached to the two support members 58A, 58B, the two second carton chucks 52 are moved toward each other with respect to their initial positions. Such movement brings the second carton chucks 52 into contact with the corresponding cartons P. The second carton chucks 52 thus hold the multiple cartons P mounted on the mounting table 14S collectively, as represented by the long dashed double-short dashed lines in FIG. 2.

In the illustrated embodiment, fall restraining members 55 are provided to enable stable separation of the first carton chucks 51 and the second carton chucks 52 from the corresponding cartons P without causing the cartons P to fall at the time the first and second carton chucks 51, 52 separate from the cartons P to return to the initial positions, thus canceling the state contacting the cartons P. That is, as illustrated in FIG. 2, each of the fall restraining members 55 has a substantially C-shaped cross section as viewed in the certain direction and is attached to the moving rods 51B, 52B such that two distal end sections 55*a* of each fall restraining member 55 are located at opposite, upper and lower, sides of the corresponding second carton chuck 52. The distal end sections 55*a* of each fall restraining member 55 contact a carton P while being elastically deformed by a predetermined amount. Until the second carton chuck 52 separates from the carton P after deactivation of the second actuators 52A, such amount of elastic deformation allows the fall restraining member 55 to maintain the state contacting the carton P.

Next, inspecting operation of cartons P, which is performed by the container inspection device 11, will be described with reference to the operation flow represented in FIG. 3. In the illustrated embodiment, inspecting operation for excessive trapped air in the cartons P is carried out. The inspecting operation is executed by a non-illustrated controller by controlling operation of drive sources for moving the transfer 15, the mounting table 14, and the like and controlling actuation of the vacuum pump and actuators in a period until conveying of cartons P by the inlet conveyor 12 is switched to conveying of the cartons P by the outlet conveyor 13.

With reference to FIG. 3, cartons P are conveyed by the inlet conveyor 12 in Step S1. Then, in Step S2, the carton stopper 20 is moved to project upward. Through such projecting movement of the carton stopper 20, the carton stopper 20 stops movement of the cartons P in the certain direction, which are conveyed by the inlet conveyor 12 in the certain direction. As a result, a consecutively increasing number of cartons P are stopped from moving in the conveying direction (the certain direction) and aligned in a continuous row in the certain direction on the inlet conveyor 12.

Subsequently, in Step S3, the continuous-row detecting portion 23 detects a continuous row formed by a predetermined number of cartons P. Then, in Step S4, the constant-amount stoppers 25 and carton chucks are moved. In this step, the four second actuators 52A at the downstream side in the certain direction are maintained without actuation but the four first actuators 51A, which are located upstream from the second actuators 52A, are actuated. The two first carton chucks 51 are thus moved toward each other from their initial positions to clamp (hold) the continuous row of cartons P on the inlet conveyor 12 collectively.

Then, with the two first carton chucks 51 clamping the multiple cartons P collectively as indicated in Step S4, the carton stopper 20 is retracted to return to the initial position in the subsequent Step S5. Afterwards, in Step S6, the transfer 15 is advanced. Further, the constant-amount stoppers 25 are retracted to return to the initial positions in Step S7.

Referring to FIGS. 4(*a*), 4(*b*), and 4(*c*), the state of the container inspection device 11 during the inspecting operation from Step S1 to Step S7 will hereafter be described. Each of the drawings illustrates the components of the container inspection device 11 schematically with a plan view and a front view shown at the left side and the right side, respectively, of the sheet surface.

FIG. 4(*a*) represents the state of the container inspection device 11 brought about by the operation through Step S2. As represented by the blank arrow in the drawing, multiple cartons P are conveyed by the inlet conveyor 12 in the certain direction, which extends from the left side to the right side of the sheet surface, at a set speed in a state spaced apart. At this time, the constant-amount stoppers 25, the first carton chucks 51, and the second carton chucks 52 are maintained, without moving, at the respective initial positions, which are separate from the cartons P. The first carton chucks 51 are located at the positions corresponding to the inlet conveyor 12 in the certain direction. The second carton chucks 52 are located at the positions corresponding to the mounting table 14 in the certain direction. The carton stopper 20 is held in a lifted state. The mounting table 14 is maintained in a lowered state without being lifted by the lift mechanism 40.

FIG. 4(*b*) represents the state of the container inspection device 11 brought about by the operation through Step S4. The cartons P are aligned in a continuous row in the certain direction on the inlet conveyor 12 and maintained in a state clamped and held by the constant-amount stoppers 25 and the first carton chucks 51, which have moved as represented by the solid arrows. Specifically, the first carton chucks 51 hold fourteen cartons P and the constant-amount stoppers 25 hold two cartons P. The mounting table 14 is maintained in the lowered state.

FIG. 4(*c*) represents the state of the container inspection device 11 brought about by the operation through Step S7. Through advance of the transfer 15 represented by the corresponding solid arrow in the drawing, the cartons P held by the first carton chucks 51 are moved onto the mounting surface 14S of the mounting table 14. Specifically, by the time the transfer 15 starts to advance, the carton stopper 20 is moved to the initial position not to project upward with respect to the belt surface of the conveyor belt 21.

Such advance of the transfer 15 moves the second carton chucks 52 from the positions corresponding to the mounting table 14 to the positions corresponding to the outlet conveyor 13 in the certain direction. Also, the constant-amount stoppers 25 are moved to the initial positions as represented by the corresponding solid arrows in FIG. 4(*c*). This switches the cartons P, which have been clamped and held by the constant-amount stoppers 25, to a state in which the cartons P are conveyed by the inlet conveyor 12 in the certain direction.

With reference to FIG. 3, following Step S7, Steps S1 to S3 are repeatedly performed while the carton chucks are retracted in Step S8. Specifically, the first carton chucks 51 are retracted to the initial positions to separate from the cartons P, thus releasing the cartons P from the held state. Subsequently, in Step S9, the transfer 15 is retracted.

Meanwhile, following operation of releasing the cartons P from the held state by the first carton chucks 51 (Step S8), Steps S11 to S14 are performed while Step S9 is carried out. That is, the mounting table 14 is lifted in Step S11. This causes the mounting surface 14S to contact the chamber portion 16 and close the opening 16K such that the receiving space SK in the chamber portion 16 becomes the sealed space. Then, in Step S12, the receiving space SK in the chamber portion 16 is depressurized. In the illustrated embodiment, the displacement sensor 60 detects the displacement amount of each of the opposite side surfaces of a carton P that expands due to the aforementioned depressurization. In this manner, the cartons P are inspected for excessive trapped air inside each of the cartons P. After such inspection is completed, the receiving space SK is released from the depressurization in Step S13. Subsequently, in Step S14, the mounting table 14 is lowered.

Then, in the container inspection device 11 of the illustrated embodiment, in a state in which retraction of the transfer 15 (Step S9) and lowering of the mounting table 14 to the initial position (Step S14) are both completed, the operation re-proceeds from Step S3 to Step S4 such that the constant-amount stoppers 25 and the carton chucks are moved. Specifically, the four first actuators 51A and the four second actuators 52A are actuated altogether. The two first carton chucks 51 and the two second carton chucks 52 are thus moved toward the opposing carton chucks 51, 52. Following Step S4, the carton stopper 20 is retracted in Step S5.

Referring to FIGS. 5(*a*), 5(*b*), and 5(*c*), the state of the container inspection device 11 during the inspecting operation after Step S8, which includes Step S9 and the operation from Steps S11 to S14 as well as the inspecting operation continuing to Steps S4 and S5 that are repeatedly performed, will hereafter be described. Each of the drawings illustrates the components of the container inspection device 11 schematically with a plan view and a front view shown at the left side and the right side, respectively, of the sheet surface, as in FIGS. 4(*a*), 4(*b*), and 4(*c*).

FIG. 5(*a*) represents the state of the container inspection device 11 brought about by the operation through Step S8. After having been moved from the inlet conveyor 12 to the mounting surface 14S of the mounting table 14 through advance of the transfer 15, the cartons P are mounted onto the mounting surface 14S (specifically, the groove portion 14M of the mounting surface 14S) when the first carton chucks 51 are retracted to the initial positions as represented by the solid arrows in the drawing and thus separate from the cartons P. Meanwhile, the inlet conveyor 12 continuously conveys cartons P in the certain direction. At this time, the carton stopper 20 is in a lifted state as indicated by Step S2, which is re-performed after Step S7.

FIG. 5(*b*) represents the state of the container inspection device 11 brought about by the operation through Steps S9 and S11. The transfer 15, which has advanced in the certain direction, is retracted as represented by the broken arrow in the drawing and returned to the initial position where the transfer 15 had been located before advancing. Also, the mounting table 14 is lifted from the initial position by the lift mechanism 40. With the mounting table 14 held in the lifted state, the receiving space SK is depressurized (Step S12) and then released from such depressurization (Step S13).

FIG. 5(*c*) represents the state of the container inspection device 11 brought about by the operation through Step S4 and S5, which is re-performed. Cartons P are in a continuous row in the certain direction on the inlet conveyor 12 and clamped and held by the constant-amount stoppers 25 and the first carton chucks 51, which have been moved as represented by the corresponding solid arrows. The carton stopper 20 is moved not to project upward with respect to the belt surface of the conveyor belt 21.

In the re-performed operation of Step S4, while the first carton chucks 51 and the constant-amount stoppers 25 are moved, the second carton chucks 52 are also moved as represented by the corresponding solid arrows. That is, multiple (in this case, fourteen) cartons P on the inlet conveyor 12 are clamped and held collectively by the two first carton chucks 51. Meanwhile, multiple (in this case, fourteen) cartons P after inspection are clamped and held collectively by the two second carton chucks 52.

Referring to FIG. 3, following Step S5, which has been re-performed, the transfer 15 is advanced in Step S6 and the constant-amount stoppers 25 are retracted in Step S7. After Step S7, Steps S1 to S3 are re-executed while the carton chucks are retracted in Step S8. Specifically, the first carton chucks 51 and the second carton chucks 52 are retracted to the initial positions to separate from the corresponding cartons P, thus releasing the cartons P from the held state. In this manner, the cartons P are mounted onto the mounting table 14 and the cartons P after inspection are mounted onto the outlet conveyor 13.

Following the re-performed Step S8, Step S9 and the operations from Steps S11 to S14 executed simultaneously with Step S9, as well as Step S10 in which the cartons P are conveyed by the outlet conveyor 13, are carried out.

With reference to FIGS. 6(*a*), 6(*b*), and 6(*c*), the states of the container inspection device 11 that are brought about by Step S6 to Steps S9 and S11, which are re-performed following Step S5, and by Step S10, will hereafter be described. Each of the drawings illustrates the components of the container inspection device 11 schematically with a plan view and a front view shown at the left side and the right side, respectively, of the sheet surface, as in FIGS. 4(*a*), 4(*b*), and 4(*c*).

FIG. 6(*a*) represents the state of the container inspection device 11 brought about by Step S6, which is re-executed. As the transfer 15 advances as represented by the corresponding solid arrow in the drawing, the cartons P held by the first carton chucks 51 are moved onto the mounting surface 14S of the mounting table 14. Meanwhile, the cartons P held by the second carton chucks 52 are moved onto the outlet conveyor 13. By this time, the constant-amount stoppers 25 are moved to the initial positions as represented by the corresponding solid arrows in the drawing. This allows the cartons P to be conveyed in the certain direction by the inlet conveyor 12.

FIG. 6(*b*) represents the state of the container inspection device 11 brought about by Step S8 and the operation through Step S2, which are re-executed. After having been moved from the inlet conveyor 12 to the mounting surface 14S of the mounting table 14 through advance of the transfer 15, the cartons P are mounted onto the mounting surface 14S (specifically, the groove portion 14M of the mounting surface 14S) when the first carton chucks 51 are retracted to the initial positions as represented by the corresponding solid arrows in the drawing and thus separate from the cartons P. Meanwhile, the carton stopper 20 is in a lifted state as indicated by Step S2, which is performed after Step S7. The cartons P that have been moved from the mounting table 14 to the outlet conveyor 13 are conveyed in the certain direction represented by the blank arrow in FIG. 6(*b*) through movement of the conveyor belt 31 of the outlet conveyor 13.

FIG. 6(*c*) represents the state of the container inspection device 11 brought about by the operation through Steps S9 and S11, which are re-executed. The transfer 15, which has advanced in the certain direction, is retracted as represented by the broken arrow in the drawing and returned to the initial position where the transfer 15 has been located before advancing. Also, the mounting table 14 is lifted from the initial position by the lift mechanism 40. With the mounting table 14 held in the lifted state, the receiving space SK is depressurized (Step S12) and then released from such depressurization (Step S13).

In Step S10, after conveying of the cartons P is started with the cartons P held in the continuous row, the stabilizer 35 causes the cartons P to be conveyed in the certain direction in the state spaced apart. Then, at a position downstream from the stabilizer 35 in the conveying direction, a carton P that has been determined to have excessive trapped air is discharged from the conveyor belt 31 of the outlet conveyor 13 into the discharge case 32*c* by means of the blasting portion 32*b* of the carton discharge mechanism 32.

As represented by the operation flow of FIG. 3, after performing Step S3, the container inspection device 11 repeats Step S4 and its subsequent steps in a state in which both Step S9 and Step S14 have been completed. That is, the container inspection device 11 repeatedly performs the inspecting operation in which the cartons P are repeatedly switched from the state illustrated in FIG. 6(*c*) to the state of FIG. 5(*c*), the state of FIG. 6(*a*), and the state of FIG. 6(*b*) sequentially and then returned to the state of FIG. 6(*c*).

By repeating such inspecting operation, the transfer 15 conveys the cartons P conveyed by the inlet conveyor 12 to the mounting table 14 and, simultaneously, conveys the cartons P after inspection mounted on the mounting table 14 to the outlet conveyor 13, collectively, in the certain direction at a high speed. Then, out of the cartons P after inspection conveyed to the outlet conveyor 13, cartons P having excessive trapped air are discharged while being conveyed by the outlet conveyor 13.

In the illustrated embodiment, the belt surface of the conveyor belt 21, the mounting surface 14S (specifically, the groove portion 14M), and the belt surface of the conveyor belt 31 are substantially flush with one another in the vertical direction and aligned in a row in the certain direction as viewed in the vertical direction. Further, an upper end section of the mounting surface 14S of the mounting table 14 located at the trailing side in the certain direction is chamfered. This configuration enables smooth movement of cartons P from the inlet conveyor 12 to the mounting table 14 and then from the mounting table 14 to the outlet conveyor 13 when the transfer 15 moves.

The illustrated embodiment has the advantages described below.

(1) The transfer 15 conveys multiple cartons P from the inlet conveyor 12 to the mounting table 14 at a high speed and then from the mounting table 14 to the outlet conveyor 13 at a high speed. This ensures a high conveying speed of the cartons P before and after inspection of cartons P in the receiving space SK in a state mounted on the mounting table 14. The inspection time per carton P is thus decreased.

(2) The inlet conveyor 12, the outlet conveyor 13, and the mounting table 14 are aligned in a row in the certain direction. This allows the transfer 15 to convey multiple cartons P from the inlet conveyor 12 to the outlet conveyor 13 via the mounting table 14 by a minimum distance. This decreases the inspection time per carton P.

(3) The transfer 15 conveys cartons P held in a continuous row on the inlet conveyor 12 while maintaining the cartons P in the continuous row. This ensures high-speed conveying of the cartons P from the inlet conveyor 12 to the mounting table 14, without increasing the conveying speed of the cartons P by the inlet conveyor 12. The inspection time per carton P is thus decreased.

(4) The receiving space SK for cartons P is formed by moving the mounting table 14 (the mounting surface 14S), which is a plate member, without moving the chamber portion 16. This facilitates high-speed movement of multiple cartons P into the receiving space SK, compared to a case in which the chamber portion 16, which has the box-like shape, is moved. Decrease of the inspection time per carton P is thus facilitated.

(5) The mounting surface 14S of the mounting table 14 is selectively lifted and lowered in the vertical direction. When lifted, the mounting surface 14S contacts the chamber portion 16 and closes the opening 16K such that the mounting table 14 (the mounting surface 14S) and the chamber portion 16 are located at the positions layered in the up-down direction. This restrains increase of the surface area occupied by the container inspection device 11 in a horizontal direction and decreases the inspection time per carton P.

The illustrated embodiment may be modified to the other embodiments described below.

In the illustrated embodiment, the mounting surface 14S of the mounting table 14 does not necessarily have to be selectively lifted and lowered in the vertical direction. For example, the mounting table 14 may be adapted to be reciprocated in a direction inclined with respect to the vertical direction or in a horizontal direction crossing the conveying direction. In these cases, it is preferable to form the chamber portion 16 such that the opening 16K of the chamber portion 16 faces in the direction in which the mounting table 14 (the mounting surface 14S) moves.

In the illustrated embodiment, the mounting surface 14S of the mounting table 14 does not necessarily have to be movable. For example, the chamber portion 16 may be adapted to be movable. That is, the chamber portion 16 may be adapted to move and contact the mounting surface 14S to close the opening 16K. Alternatively, both the chamber portion 16 and the mounting surface 14S may be adapted to be movable.

In the illustrated embodiment, the inlet conveyor 12 does not necessarily have to include the carton stopper 20, which stops movement of cartons P. For example, if cartons P are conveyed in a continuous row by the inlet conveyor 12, the carton stopper 20 does not have to arrange the cartons P in a continuous row. In this case, it is preferable that the transfer 15 be adapted to convey the cartons P conveyed in a continuous row by the inlet conveyor 12 to the mounting table 14 at a high speed.

In the illustrated embodiment, the inlet conveyor 12, the outlet conveyor 13, and the mounting table 14 do not necessarily have to be aligned in a row in the certain direction. For example, the inlet conveyor 12, the outlet conveyor 13, and the mounting table 14 may be arranged adjacently to form an arcuate shape. In this case, it is preferable that the transfer 15 move along the arcuate shape. In other words, the inlet conveyor 12, the outlet conveyor 13, and the mounting table 14 may be arranged in any suitable manner as long as the inlet conveyor 12, the outlet conveyor 13, and the mounting table 14 are arranged adjacently in the movement direction of the transfer 15.

In the illustrated embodiment, inspection of cartons P is not restricted to inspection for excessive trapped air. Any suitable inspection may be performed as long as the inspection is carried out with multiple cartons P collectively received in the chamber portion 16. Further, the receiving space SK in the chamber portion 16 does not necessarily have to be a sealed space.

In the illustrated embodiment, the certain direction is not restricted to a horizontal direction but may be a diagonal direction forming an acute angle with respect to a horizontal direction.

In the illustrated embodiment, neither the first nor second conveying portion is restricted to a conveyor using a belt. The first and second conveying portions may be conveyors using a chain or a roller. That is, the first and second conveying portions may be any other suitable types as long as the conveying portions are adapted to convey cartons P continuously.

In the illustrated embodiment, the transfer 15 serving as the third conveying portion does not necessarily have to be reciprocally movable in the certain direction at a speed greater than the conveying speed of cartons P by the inlet conveyor 12. For example, the speed at which the transfer 15 is retracted to the initial position after having advanced in the certain direction may be smaller than or equal to the conveying speed of cartons P by the inlet conveyor 12. Alternatively, the transfer 15 serving as the third conveying portion does not necessarily have to be adapted to be reciprocally movable. The transfer 15 may be adapted to include a rotary type movement mechanism, for example, and thus be movable only in the certain direction, which is the same direction as the movement direction of the inlet conveyor 12.

DESCRIPTION OF REFERENCE NUMERALS

11 . . . Container Inspection Device, 12 . . . Inlet Conveyor (Example of First Conveying Portion), 13 . . . Outlet Conveyor (Example of Second Conveying Portion), 14 . . . Mounting Table, 14S . . . Mounting Surface, 15 . . . Transfer (Example of Third Conveying Portion), 16 . . . Chamber Portion (Example of Receiving Case), 16K . . . Opening, 20 . . . Carton Stopper (Example of Conveying Stopping Portion), P . . . Carton (Example of Liquid Container), SK . . . Receiving Space

The invention claimed is:

1. A container inspection device that receives a plurality of conveyed liquid containers in a receiving space and inspects the containers, the device comprising:

a first conveying portion configured to convey the liquid containers containing a liquid in a certain direction;

a second conveying portion that is located downstream, relative to the certain direction of the first conveying portion, from the first conveying portion and that is configured to convey the liquid containers in the certain direction;

a mounting table that is located between the first conveying portion and the second conveying portion along the certain direction and that has a mounting surface on which multiple ones of the liquid containers can be mounted;

a receiving case having an opening in a section of the receiving case, a receiving space being formed in the receiving case when the mounting surface contacts the receiving case to close the opening; and a third conveying portion that is movable in the certain direction at a speed greater than a conveying speed of the liquid containers by the first conveying portion, wherein the third conveying portion holds multiple ones of the liquid containers that have been conveyed by the first conveying portion collectively and conveys the liquid containers to the mounting surface of the mounting table, and wherein the third conveying portion holds the multiple ones of the liquid containers mounted on the mounting surface collectively and conveys the liquid containers to the second conveying portion.

2. The container inspection device according to claim 1, wherein:

the first conveying portion, the second conveying portion, and the mounting table are aligned in a row that is parallel to the certain direction.

3. The container inspection device according to claim 1, comprising:

a conveying stopping portion that stops conveyance of the liquid containers by the first conveying portion and arranges multiple ones of the liquid containers in a continuous row in the certain direction, wherein the third conveying portion holds the multiple ones of the liquid containers in the continuous row collectively and conveys the liquid containers to the mounting surface of the mounting table.

4. The container inspection device according to claim 1, wherein:

the mounting surface of the mounting table is movable; and the mounting surface moves to contact the receiving case and close the opening, thereby forming the receiving space.

5. The container inspection device according to claim 4, wherein:

the mounting surface of the mounting table can be selectively lifted and lowered in a vertical direction; and the mounting surface is lifted to contact the receiving case having a downward opening from below, thereby closing the opening to form the receiving space.

* * * * *